(12) United States Patent
Weiss et al.

(10) Patent No.: US 7,137,309 B2
(45) Date of Patent: Nov. 21, 2006

(54) HIGH PRECISION GAS BEARING SPLIT-AXIS STAGE FOR TRANSPORT AND CONSTRAINT OF LARGE FLAT FLEXIBLE MEDIA DURING PROCESSING

(75) Inventors: Adam Weiss, Pickering (CA); Afsar Saranli, Toronto (CA); Eduardo Ghelman, Etobicoke (CA); David Baldwin, Atascadero, CA (US)

(73) Assignee: Photon Dynamics, Inc., San Jose, CA (US)

( * ) Notice: Subject to any disclaimer, the term of this patent is extended or adjusted under 35 U.S.C. 154(b) by 0 days.

(21) Appl. No.: 11/249,039

(22) Filed: Oct. 11, 2005

(65) Prior Publication Data

US 2006/0096395 A1 May 11, 2006

Related U.S. Application Data

(62) Division of application No. 10/637,215, filed on Aug. 8, 2003.

(51) Int. Cl.
*G01B 11/30* (2006.01)
*G01B 21/30* (2006.01)
*B65G 49/05* (2006.01)
*H01L 21/677* (2006.01)

(52) U.S. Cl. ............. 73/865.8; 198/502.3; 414/222.02; 414/222.04

(58) Field of Classification Search ............... 73/865.8; 198/502.1–502.4; 414/222.01–226.05, 676
See application file for complete search history.

(56) References Cited

U.S. PATENT DOCUMENTS 4,534,695 A * 8/1985 Stump et al. ............... 219/386
4,730,526 A 3/1988 Pearl et al.
5,016,363 A 5/1991 Krieger
5,056,765 A 10/1991 Brandstater
5,141,212 A 8/1992 Beeding
5,290,134 A * 3/1994 Baba .......................... 414/404
5,307,011 A * 4/1994 Tani .......................... 324/158.1
5,374,021 A 12/1994 Kleinman
5,384,531 A * 1/1995 Yamazaki et al. .......... 324/765
5,701,178 A * 12/1997 Burns et al. ................. 356/600
5,797,317 A 8/1998 Lahat et al.

(Continued)

FOREIGN PATENT DOCUMENTS

JP      2002267571 A  *  9/2002

(Continued)

OTHER PUBLICATIONS

"Arraychecker 3000" to PhotonDynamics, available on the Internet at <http://www.photondynamics.com>.*

(Continued)

*Primary Examiner*—Hezron Williams
*Assistant Examiner*—David A. Rogers
(74) *Attorney, Agent, or Firm*—Townsend and Townsend and Crew LLP

(57) ABSTRACT

A modular split-axis stage is used to inspect and/or repair large flat glass media suitable for LCD/TFT applications. Low-precision air table sections are detachably mounted to a centrally located, high-precision granite inspection/repair section. Glass media held by a vacuum contact is transported on air cushions from the up-web air table to the central inspection/repair section. Vacuum nozzles integrated with porous medium pads precisely control the height of the flexible media above the central section during inspection or repair. Embodiments includes structures in which the media is either stationary or moving during inspection/repair. A first media can be loaded/unloaded while a second media is undergoing inspection or repair in a pipelined operational mode.

11 Claims, 12 Drawing Sheets

U.S. PATENT DOCUMENTS

| | | |
|---|---|---|
| 5,913,268 A | 6/1999 | Jackson et al. |
| 6,145,648 A | 11/2000 | Teichman et al. |
| 6,217,272 B1 * | 4/2001 | Felsenthal et al. .......... 414/217 |
| 6,223,880 B1 | 5/2001 | Caspi et al. |
| 6,281,655 B1 * | 8/2001 | Poon et al. ................. 318/649 |
| 6,367,609 B1 | 4/2002 | Caspi et al. |
| 6,442,369 B1 | 8/2002 | Swartz et al. |
| 6,486,927 B1 | 11/2002 | Kim |
| 6,486,941 B1 * | 11/2002 | Hazelton et al. .............. 355/72 |
| 6,675,666 B1 * | 1/2004 | Maruyama et al. ........ 73/865.8 |
| 6,906,546 B1 * | 6/2005 | Tanioka et al. ............. 324/765 |
| 2004/0028113 A1 * | 2/2004 | Schlagheck et al. .......... 374/57 |
| 2004/0086166 A1 * | 5/2004 | Weiss et al. ................. 382/141 |
| 2004/0109598 A1 * | 6/2004 | Weiss et al. ................. 382/141 |

FOREIGN PATENT DOCUMENTS

| | | | |
|---|---|---|---|
| JP | 2002365026 A | * | 12/2002 |
| KR | 358704 B | * | 10/2002 |
| KR | 358707 B | * | 10/2002 |

OTHER PUBLICATIONS

"Arraychecker 3500" to PhotonDynamics, available on the Internet at <http://www.photondynamics.com>.*

* cited by examiner

HIGH PRECISION GAS BEARING SPLIT-AXIS STAGE FOR TRANSPORT AND CONSTRAINT OF LARGE FLAT FLEXIBLE MEDIA DURING PROCESSING

CROSS-REFERENCES TO RELATED APPLICATIONS

This application is a divisional of U.S. patent application Ser. No. 10/637,215 filed Aug. 8, 2003.

BACKGROUND OF THE INVENTION

This invention relates to methods and apparatus for handling large flat and generally very thin flexible objects, and specifically to methods and apparatus for transporting, supporting, positioning, and constraining, with high mechanical precision, large flat flexible media. More specifically, this invention relates to the use of such transport and constraint mechanisms and techniques for automated optical inspection (AOI), electrical functional inspection (e.g., Voltage Imaging or VI) or automated repair (AR) of large flat, flexible and possibly patterned media, such as glass panels deposited with structures used to form thin film transistor (TFT) arrays (which are the main active component of liquid crystal flat panel displays (LCD). Although the invention is applicable to the general case of inspection of any flat flexible media, it is particularly useful for the high throughput, in-line inspection of glass plates of TFT/LCD panels at various stages of production.

During the manufacturing of LCD panels, large clear sheets of thin glass are used as a substrate for the deposition of various layers of materials to form electronic circuits that are intended to function as a plurality of separable, identical display panels. This deposition is usually done in stages where in some stages, a particular material (such as metal, Indium Tin Oxide (ITO), Silicon, Amorphous Silicon etc.) is deposited over a previous layer (or upon the bare glass substrate) in adherence to a predetermined pattern. Each stage may also include various other steps such as deposition, masking, etching, and stripping.

During each of these stages, and at various steps within a stage, many production defects may occur, that have electronic and/or visual implications on the final performance of the LCD product. Such defects include but, are not limited to: circuit shorts, opens, foreign particles, miss-deposition, feature size problems, over and under etching. The most common defects, shown in FIG. 1, include: metal protrusion 110 into ITO 112, ITO protrusion 114 into metal 116, a so-called mouse bite 118, an open circuit 120, a short 122 in a transistor 124, and a foreign particle 126.

In the preferred application domain such as the inspection and repair of TFT LCD panels, the defects subject to detection and repair can be as small as several microns in size, placing demanding defect detection limits on inspection and repair systems. Moreover, mere detection of defects is insufficient. Detected defects must also be classified as process defects, i.e. minor imperfections which do not undermine the performance of the finished product but are an early indication of the array manufacturing process drifting out of optimum conditions; reparable defects, which can be repaired, thus improving the array production yield; and finally killer defects, which disqualify the TFT array from further use.

Achieving this level of detection and classification often requires a two stage imaging process. An initial comparatively low resolution imaging process is used in a fast detection mode to detect a number of points of interest—POI (or defect candidates) over the entire surface inspected. A second comparatively high resolution imaging process is used to review and further image these POIs as part of a high resolution image analysis and classification process. Such systems require a very high degree of mechanical precision as will be explained below in relation to FIGS. 2 and 3.

FIG. 2 illustrates the six degrees of freedom for any object in motion in three-dimensional space: namely, linear motion along the three orthogonal axes as well as rotation around any of these axes. This framework is valid for all moving elements in a typical surface inspection system. Motion along each of these degrees of freedom may be intentional (due to actuation) or unintentional (due to mechanical inaccuracy in the system). For example, as an object is linearly translated along the y-axis, there may be a uncontrolled roll around the y-axis, a yaw around the z-axis, and a pitch around the x-axis. Usually, a mechanical stage translates or rotates an object along selected degrees of freedom while attempting to constrain the object from translating or rotating along the remaining ones. However, due to the inability to achieve perfect mechanical control, the uncontrolled movements along any of these remaining degrees of freedom lead to the system exhibiting a reduced mechanical precision. The mechanical precision of such a system can often be characterized by the accuracy, the repeatability, and the resolution. Accuracy measures how closely a mechanical positioning system can approach the instructed target position in the steady state. The repeatability on the other hand, measures how close the final steady state positions are to each other on repeated attempts to move to the same target position, possibly from different initial positions. The resolution is defined as the smallest incremental motion possible along a given degree of freedom.

FIGS. 3A and 3B illustrate a simplified example inspection system for large area flat media, which is one focus of the present invention. The system may be transformed into a repair instrument by changing the payload on the illustrated gantry 316. In this particular configuration, a low and high-resolution optical inspection task is explained. In a typical system, there are multiple low-resolution inspection cameras (typically each with 3.0–15.0 μm/pixel object plane resolution) that are part of a low resolution system 312 and one or more high resolution inspection cameras (typically each with 0.5–1.0 μm/pixel object plane resolution) that are part of a high resolution system 310.

Flat media 318 under inspection is transported over a precision surface 320 approximating a plane with tight flatness specifications. For example, ±2.0 μm z-axis variation over 1 m is achievable. The low resolution imaging system 312 and the high resolution imaging system 310 are mounted by means of precision gantry 316 over the surface. The mechanical stage is designed so that either of the imaging systems can be used to image any arbitrary point on the media surface 318. Furthermore, the imaging system requirements, such as focal length and depth of field dictate that the distance from the imaging system to the surface is controlled during the imaging process to within 1.0 μm to assure that the depth of field limitation of ±1.5 μm is not violated. There are multiple means of achieving this positional control. For example, one can let both imaging modules remain stationary in the x-axis and y-axis and move the media to be inspected 318 over the surface 320 while having z-axis actuation on the imaging modules to control focus. An alternative is to have only y-axis motion on the media to be inspected while incorporating x-axis and z-axis actuation into the imaging modules. Still another alternative is to have the media to be inspected completely stationary while having a moving gantry 316 over the surface 320. Note that each of these configurations will shift the precision requirements onto another part of the stage, will impact the size of the stage and will also result in a particular distribution of mechanical complexity within the system.

To illustrate how mechanical precision affects the system operation, assume that the system operation consists of the x-axis and y-axis scanning motion 322 of the media to be inspected over the surface 320. Also assume the typical configuration of a line scan low resolution imaging module and an area scan high resolution imaging module. In such an inspection system, the following requirements on mechanical precision are present:

The field-of-view (FOV) of both the low resolution and the high resolution imaging modules, combined with the need to cover the entire surface of the media in multiple passes, necessitates high resolution for the x-axis position control and very high rotational stiffness around the z-axis. For example, 0.5 µm/pixel high resolution imaging using a particular line-scan camera would result in 0.4 mm x-axis FOV. This in turn would require a defect point of interest to be positioned with better than ±0.1 mm positional accuracy to within the camera FOV. The time-domain-integration (TDI) line scan imaging devices often used in low illumination intensity applications also require a consistent y-axis scanning speed to prevent image blurring. For example, a 96 stage TDI camera for a fixed integration time would suffer from one pixel image blurring from approximately 1% speed variation along the direction of scan The limited depth of field of the imaging systems, in particular for the high resolution imaging module, requires that the distance from the inspected surface to the imaging module be tightly controlled. This distance is, for example, ±1.5 µm for a typical high resolution system with 0.5 µm object plane resolution. This requires tight accuracy and repeatability in z-axis positioning and high rotational stiffness around the x and y-axes.

In order to dispatch the high resolution imaging module to the POIs indicated by the low resolution imaging module, high accuracy and repeatability is required for the x-axis and y-axis motion. Also, there should be a known stable positional relationship between the low and high resolution modules.

In practice, apart from the aforementioned positional accuracy and repeatability requirements, there may be more complex relationships involved. For example, in an optical imaging system, any misalignment of the optical axis from vertical may cause a z-axis positional change to affect the x-axis and y-axis positioning accuracy of the field of view of the imaging module.

When an application requires a high mechanical precision, the widely adopted method of providing this precision is to use a massive granite base plate and associated stiff gantry (often from granite) supporting a rigid chuck. Over the reference flat surface provided by the granite, the chuck is levitated on air bearings and is actuated by means of linear servo motors and linear encoders. The chuck usually uses vacuum as the means to constrain the media being processed to the chuck surface. This approach has been especially used for the inspection of silicon wafer integrated circuits and has also been adopted for the inspection and repair of the glass plates deposited with TFT/LCD panels.

In this configuration, the precision machined granite base plate and stiff gantry provide a precision reference frame with high stiffness and flatness. The vacuum chuck holds the flexible media to be inspected and imposes the required flatness constraints. The chuck performs a precisely controlled motion over the granite support surface. Air bearings are the best known means of constraining free movement into a single axis. They provide an inherent averaging property due to the fact that the moving shuttle does not exactly follow the imperfections of the supporting guide but on the air cushion, which produces averaging. This results in much lower linear and angular errors for the shuttle as compared to the errors implied by those supporting surfaces. The linear servo motors in combination with linear encoders provide the necessary motion precision along the actuated motion axis.

This x-y-z stage configuration employing a granite base plate, vacuum chucks, air bearings, and linear encoders is a stable platform and is adequate for numerous applications. It has been successfully used in AOI and in electrical functional inspection of silicon wafer integrated circuits, which is believed to be the most demanding application domain. Although the concept has also been extended to the AOI and electrical functional inspection of the glass plates deposited by TFT/LCD panels, limitations in this particular domain have been the weight and size. The maximum feasible size achievable by this configuration is primarily limited by the weight and size of the required monolithic granite base plate which can be feasibly manufactured, stored, transported and installed.

In the primary application domain of interest, the inspection of TFT/LCD glass plates, the size of the glass plates is constantly increased as the industry strives for larger and thinner glass. With the increased size of the media to be inspected, the needed size of the stage to transport, position, and constrain the media grows proportionally. For Generation 5 (~1,100 mm×1,300 mm glass) plate sizes, the direct scaling of the aforementioned configuration gradually ceases to be feasible. This is due to the weight, shape, and size of the instrument, which exceed the typical truck and plane cargo space capacity. (e.g., the maximum allowance for the bulk load of a commercial cargo plane is approximately seven tons while the for Generation 6 (~1,500 mm×1,850 mm glass) plate sizes, the weight of the stage is predicted to be 11 tons.) The result is an exponential increase in the cost of transporting the instrument to its final destination.

In the past, the conventional method of providing the necessary mechanical precision was based on techniques in the silicon wafer integrated circuit inspection application domain. However, with the increasing size of the media panels to be inspected, this approach quickly becomes impractical due to the unmanageable size of the stage and the escalating cost that arises.

In the prior art, there are many applications where conveyor systems to transport and constrain media are proposed for the purposes of inspection or other processing of flat media. These include but are not limited to:

U.S. Pat. No. 6,367,609 and U.S. Pat. No. 6,223,880 both to Caspi et al. describe a conveyor system with the aim of changing the direction of media to be processed to divert it into an inspection or processing apparatus where the media is constrained using a vacuum chuck or similar means. The patents address the issue of transporting and handling of flat media on a production line for the purposes of processing or inspection. However, the patent does not address the required complexity and precision requirements and the associated cost implications of the inspection/processing station. This is one of the primary objects of the present invention. Also, the described conveyor apparatus uses primarily belt driven actuation for transporting the media.

U.S. Pat. No. 4,730,526 to Pearl et al. describes a conveyor system for supporting and transporting sheet media for the purposes of processing of the sheet media. The invention discloses a vacuum constraining mechanism with distributed vacuum pads distributed among the conveyor so that vacuum constraint happens together with the transportation and possible processing of the sheet media. The invention is especially useful for tooling applications such as cutting and is not applicable to the present application domain because of differing precision requirements.

U.S. Pat. No. 6,145,648 to Teichman et al. describes a conveyor arrangement for the purposes of PCB inspection, where a continuous conveyor extends from a loader zone to an unloader zone and passes by an inspection zone for the purposes of inspecting the articles traveling on the conveyor. The primary feature of the described invention is to operate the loader and unloader robots in a coordinated way, avoiding disturbance of the inspection process when the article is being inspected by the inspection apparatus.

U.S. Pat. No. 6,486,927 to Kim describes an LCD module testing apparatus with an index feeding stage for transferring the LCD modules from a LCD stack to a work table mounted on a main frame of the testing apparatus. The testing system is based on aligning the LCD module, placing it on electrical probe pins, and constraining it there mechanically for performing the test. The system does not attempt to handle, test, and repair the large size media sheets on which the LCD panels are deposited and hence is not applicable to the application of the present invention.

U.S. Pat. No. 5,374,021 to Kleinman describes a vacuum holder to be particularly used in a vacuum table arrangement. The invention specifically addresses the issue that when the vacuum table area is large and a major area is not covered by the article being held by the vacuum, suction openings cause the waste of vacuum. The invention proposes vacuum openings with a valve structure, which closes when no article is present on top of the valve.

U.S. Pat. No. 5,141,212 to Beeding describes another vacuum chuck concept which uses a foam surface to support sheet media during cutting operations. The open cell foam passes the effect of vacuum from the underlying vacuum surface to the media being held and is cut by the cutting apparatus along with the media. The underlying vacuum surface is therefore kept intact during this operation.

U.S. Pat. No. 5,797,317 to Lahat et al. describes a universal chuck concept for holding plates of varying sizes. The invention uses a means to mechanically hold the plates from the edges and primarily applies to small sized plates (e.g. silicon wafers), such as those typically used in the manufacturing of semiconductor devices.

U.S. Pat. No. 5,056,765 to Brandstater describes a means to constrain the flat media being processed or inspected by the use of an immobilizing device acting from the top of the media, which presses the media down without contact using an air-cushion effect. The media is hence flattened against the inspection surface by the immobilizing device, which is still free to move with respect to the flat media and the table. The invention in particular applicable for printed circuit inspection.

Contributions from the other application domains such as paper copiers include the U.S. Pat. No. 6,442,369 to Swartz et al., which describes an air cushion means of loading the media sheets from the top. The load imposes non-contact z-axis flatness on the sheets while the sheets are pressed against a conveyor for transportation. The sheets are constrained and moved by the underlying conveyor while being free to move with respect to the air cushion load.

Another earlier invention, U.S. Pat. No. 5,016,363 to Krieger, describes a vacuum and air cushion arrangement for transporting and at the same time drying a wet continuous web of media, in particular paper. However, no attempt is made to constrain the flatness of the conveyed media.

In U.S. Pat. No. 5,913,268, Jackson et al. describe pneumatic rollers, which utilize alternating vacuum and air cushion operation to gracefully transport and transfer sheet paper media between the rollers of a processing instrument, in particular for the purposes of printing on the media.

Despite these contributions in related application domains, the primary approach to designing a high precision mechanical stage remains the monolithic granite approach. This popular approach has been in the public domain and shared by a number of manufacturers of inspection/repair systems for both silicon wafer integrated circuits as well as for glass plates deposited with TFT/LCD panels.

SUMMARY OF THE INVENTION

According to an embodiment of the present invention, in a testing or repair platform, the size of supported media plates can be scaled up while the size of a monolithic granite base plate and gantry can be scaled down while still providing precision frame and reference surfaces. To this end, a split-axis design is used, where the main media transport axis (y-axis) is partitioned into sections each with optionally different precision requirements. The present invention reduces the system inspection tact time, which is defined as the total time required by the system to load, align, process, and unload the media. (Tact time can also be interpreted as the total time required between each media sample in an in-line operation. As will be explained, the reduction in tact time is achieved utilizing a pipelining principle.)

An aim of the present invention is to overcome the size limitations and cost implications of the direct scaling of the monolithic granite base plate approach to higher generation (larger sized) media plates. The present invention is also aimed at addressing the associated loss of precision that accompanies scaling without the monolithic granite base, so that the resulting scalable—modular mechanical stage, in combination with complementary hardware/software, meets the requirements of a high performance inspection/repair application. Another aim of the present invention is to adapt inspection/repair systems to the increasing size of media and thereby provide a high performance inspection/repair system for the transport, positioning, and constraint of flat flexible media that meets industry precision requirements. The invention will be described in detail in the following detailed description in connection with the accompanying drawings.

DETAILED DESCRIPTION OF THE INVENTION

Figure 1:
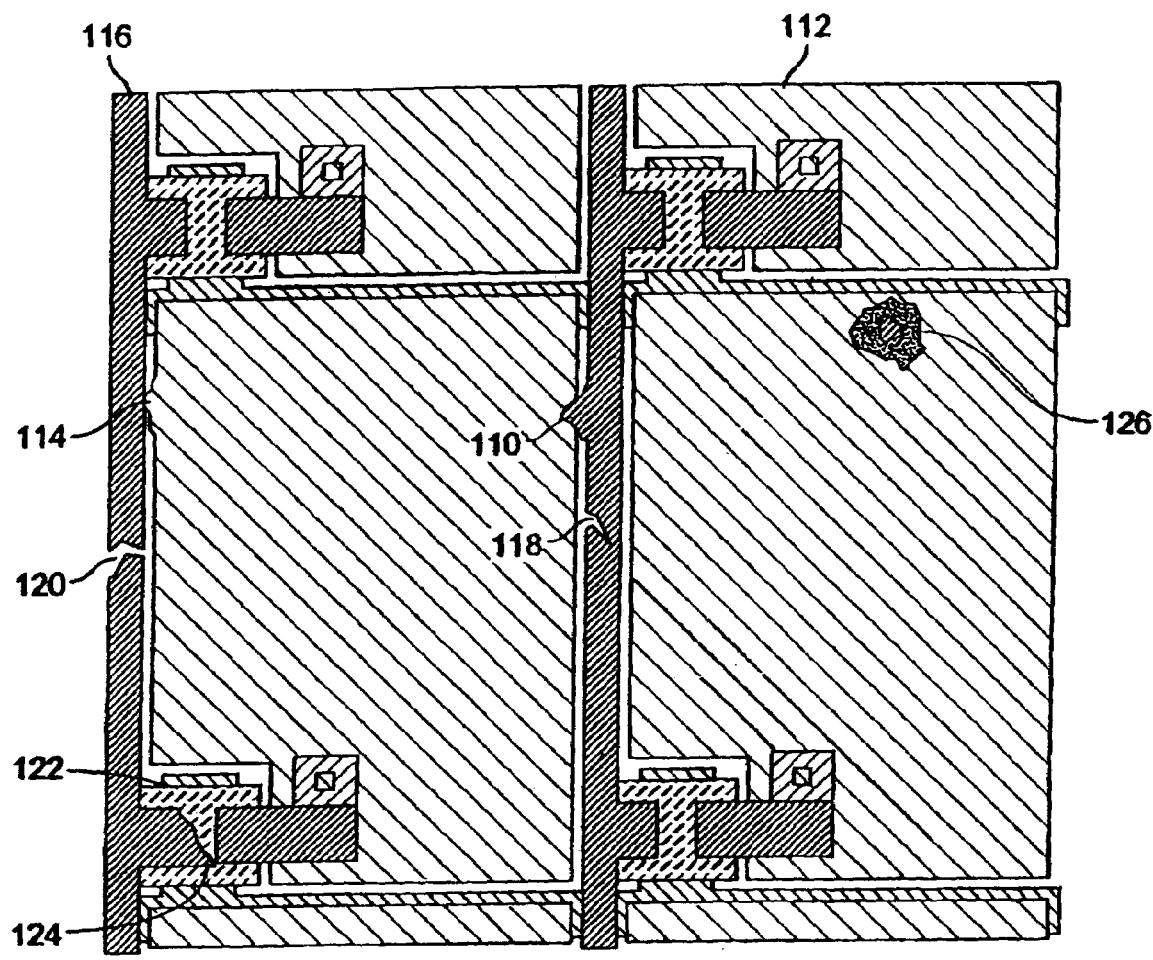
FIG. 1 is a schematic drawing of defects common to LCD panels.
Figure 2:
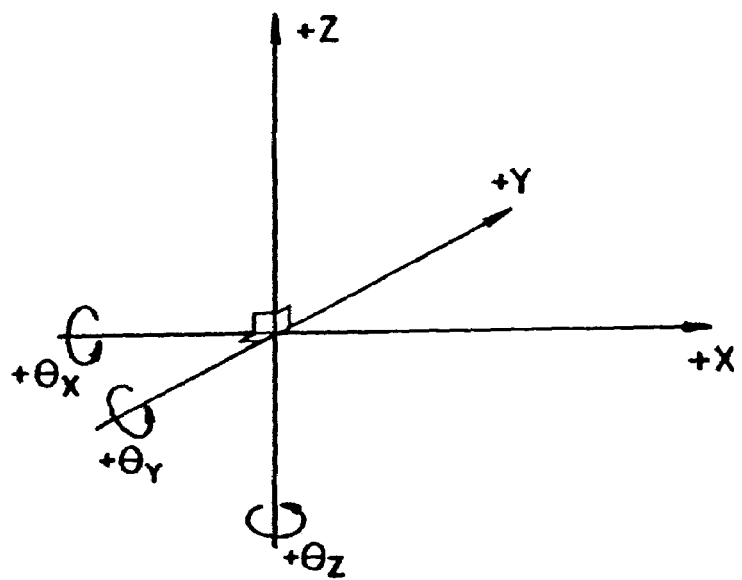
FIG. 2 is a drawing that illustrates the six degrees of freedom in three-dimensional space.
Figure 3A:
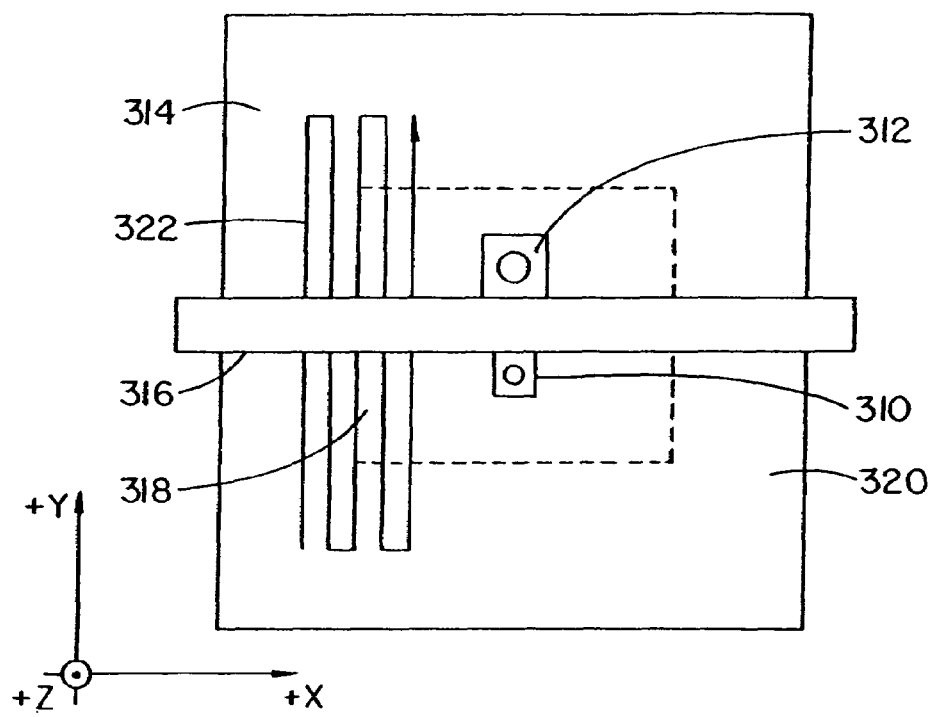
FIG. 3A is a top view of a simplified, prior art inspection system for large area flat media.
Figure 3B:
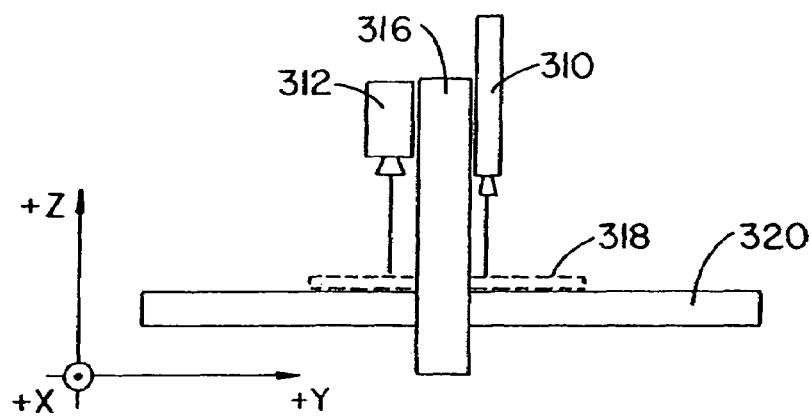
FIG. 3B is a side view of a simplified, prior art inspection system for large area flat media.
Figure 4A:
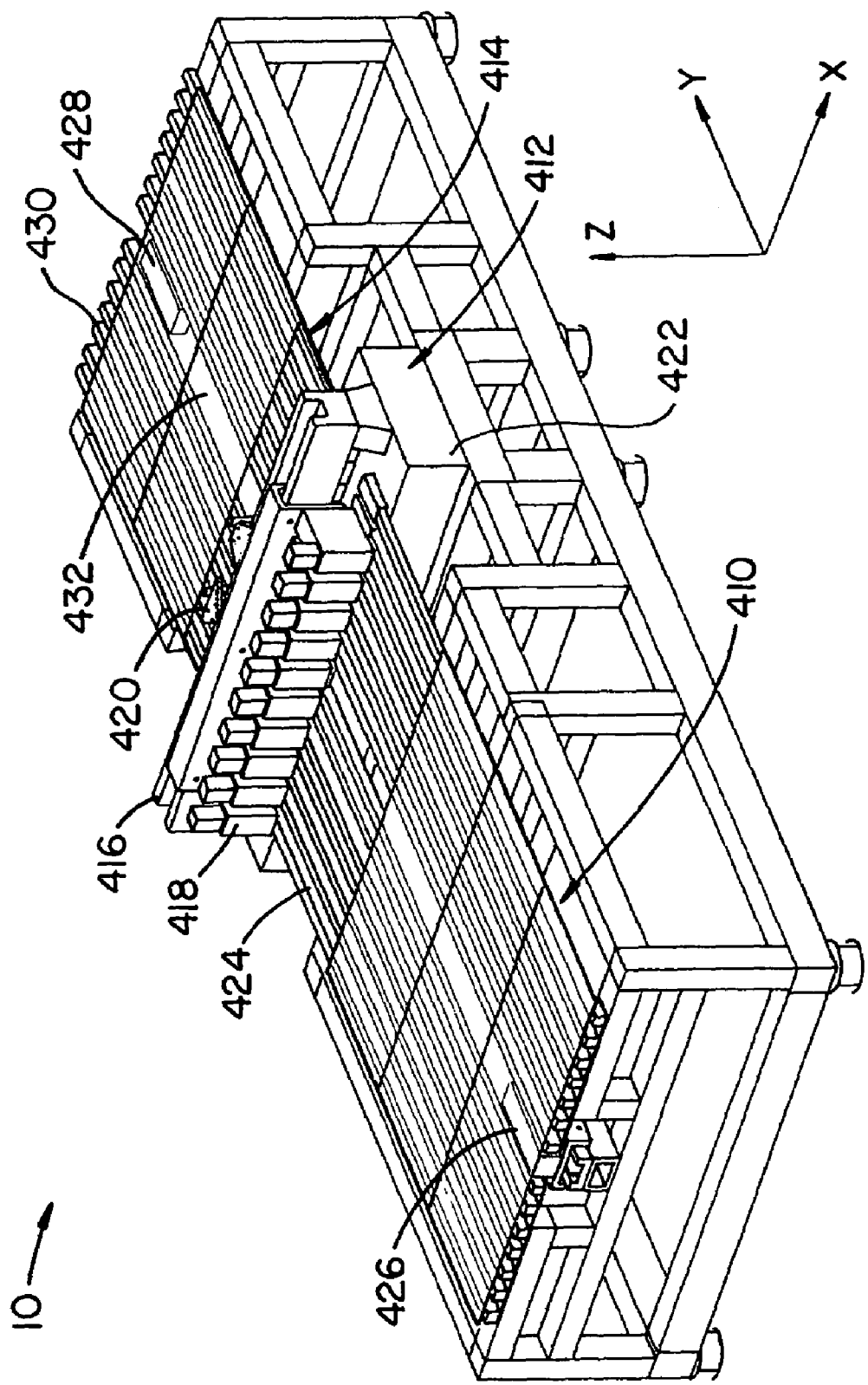
FIG. 4A is a perspective view of the first embodiment according to the invention.

Referring to FIG. 4A, the system 10 according to the invention has typically three partitions or sections 410, 412, and 414, in which the smaller size mid-web partition 412 is designed to meet the highest mechanical precision requirements for the partitions. The up-web stage partition 410 and down-web stage partition 414 are designed to support and transport flat media 432 into and out of the precision mid-web partition 412 while minimizing interference with the precision operation of the mid-web partition. An air cushion or gas bearing based flat flexible media support mechanism provided by the combined up-web, mid-web and down-web sections 410, 412, and 414 obviates the need for rigid vacuum chucks that would immobilize the media during transport and testing/repair. Only the mid-web section 412 incorporates a monolithic granite base plate surface 422 and attached gantry 416, resulting in a dramatic reduction in size and weight of the required granite block. This mid-web section holds together and properly aligns all of the critical inspection/repair components, such as imaging modules 418 and 420. It also makes it possible to precisely control the z-axis position of the media being processed during inspection/repair over surface 422. This section may have two alternative forms depending on the application mode considered, as will be detailed.

The up-web and down-web sections 410 and 414 incorporate relatively low precision air cushions 424 and 430 and do not exercise precise z-axis control over the media. Instead, they float the media 432 with a relatively larg air gap to facilitate the transition to the precision mid-web section 412 and to relax the air table tolerances. The typical thickness of the air gap used by these stages is 50–100 μm. The up-web and down-web sections 410 and 414 also incorporate vacuum contacts 426 and 428 to move the glass along the y-axis. The vacuum contacts have high torsional stiffness around the z-axis. These oversized up-web and down-web stage sections and their interface with the precision mid-web section also incorporate a pipelined mode of operation wherein the contacts operate independently but in coordination. This allows for new media to be loaded onto the system and prepared for inspection while the inspection of the previous media is still in progress. Additionally, the previously inspected media may be unloaded while the inspection of new media has already started.

A contribution of the present invention is a dramatic reduction in the size of the monolithic precision granite base plate that is required to support an inspection/repair system for large flat flexible media, for example, Generation 5 and larger TFT/LCD glass plates. Such a system is especially useful in the specific application domains used in the manufacturing of the TFT/LCD panels: automated optical or electro-optical inspection, repair of media sheets (often glass) with material deposited on the sheets, or simple automated optical inspection of plain media sheets.

In the past, designers worked off the assumption that uniform precision and accuracy were required at all points on the surface of the test sample/instrument. By contrast, the present invention demonstrates that the cost/size (and hence the feasibility) of the inspection/repair system can be controlled by limiting the spatial extent of the instrument precision. In other words, by carefully controlling the mechanical precision of the instrument in those regions where the various modes of precision are truly necessary, the required precision can be achieved by an instrument much lighter and less costly than from traditional instruments.

Figure 4B:
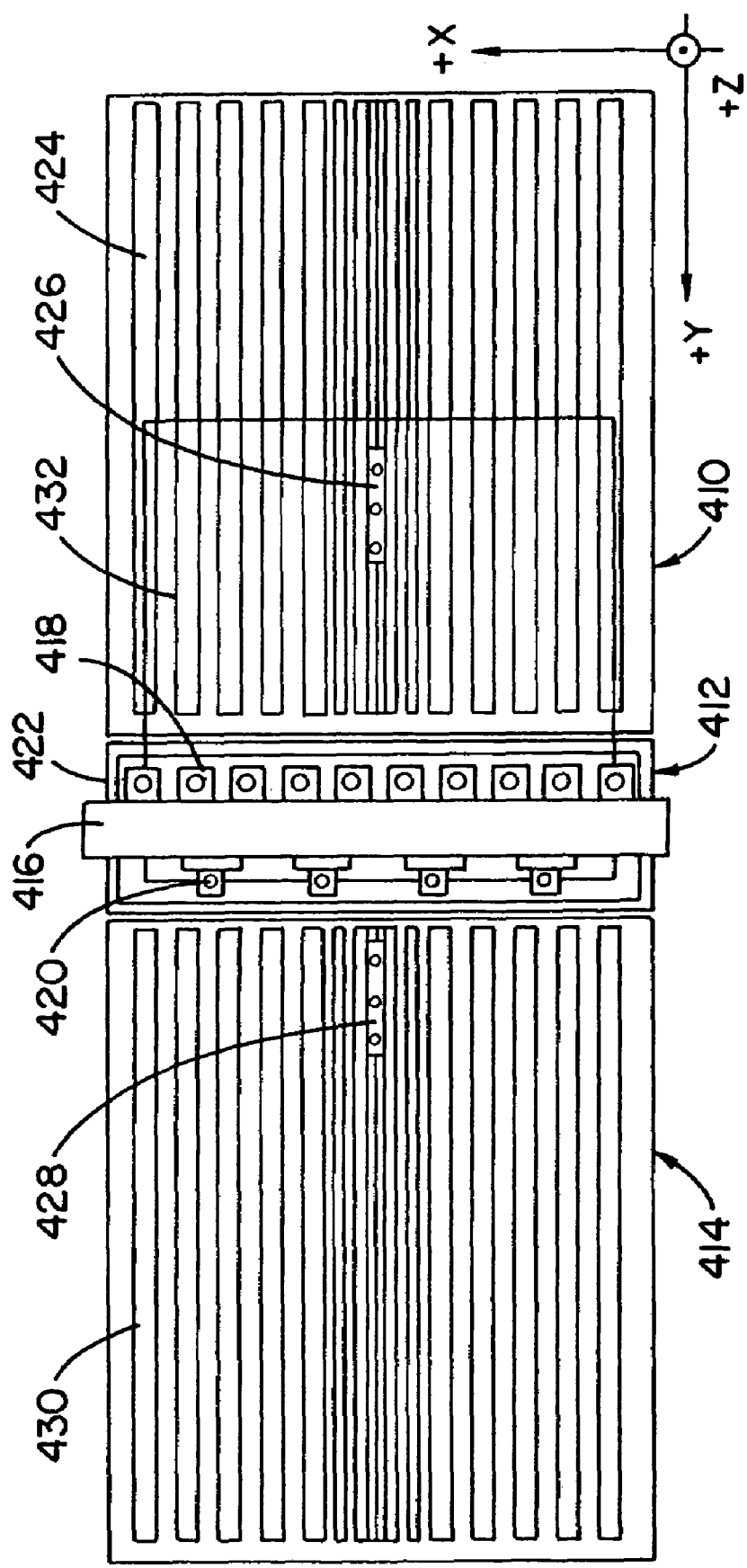
FIG. 4B is a top view of the first embodiment according to the invention.

Reference is made to FIGS. 4A and 4B, where the overall structure of an embodiment of the instrument is presented. One feature of the present invention is that the y-axis of motion is partitioned into three sections 410, 412, and 414 as previously identified. Different precision requirements are imposed on these three sections. In particular, the up-web section 410 and down-web section 414 are designed to support the media being inspected 432 with considerably relaxed tolerances for the z-axis position as well as for the x-axis and y-axis rotational alignment. These sections are responsible for contacting the media and transporting it into and out of the inspection region 412, while also moving it during the inspection process. The mid-web section 412, on the other hand, incorporates a precision-machined monolithic granite base plate supporting the precision-machined inspection surface 422. The gantry 416 holding the imaging modules 418 and 420 is usually made of granite as well, but may also be manufactured from high rigidity ceramic materials. This mid-web section 412 is designed for the highest possible precision, facilitating the steady alignment of all critical components as well as the provision of a flat reference surface for the inspection/repair modules. Therefore, alignment and calibration between the multiple low and high-resolution imaging modules and between these modules and the inspection surface can be maintained with high precision. This precision granite mid-web section is considerably smaller than both the footprint of the inspection instrument and the area of the media being inspected/repaired.

Figure 4C:
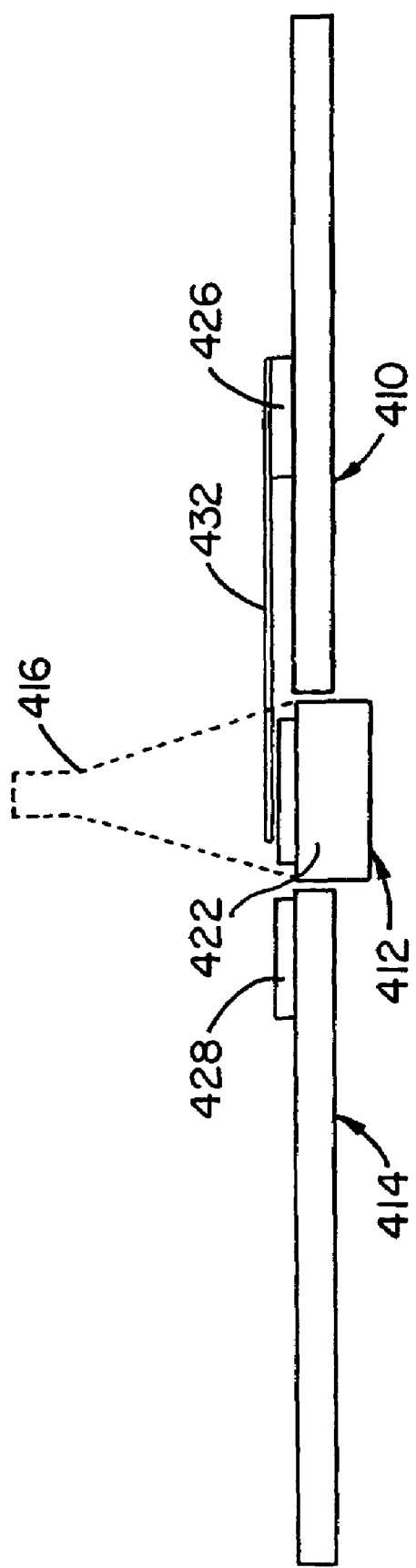
FIG. 4C is a side cross-sectional view of the device of FIG. 4A.

For purposes of this design, it is assumed that the inspected/repaired media properties are such that the flat media possesses high rigidity in the plane of the media (the x-y plane) while still possessing flexibility in the direction perpendicular to the plane of the media (the z-axis). Therefore, the media is characterized as being substantially planar while also being flexible in the z direction. This is an assumption which is valid for the primary application domain of interest. The rigidity of the media in the plane of the media enables the media to be contacted and moved with a comparatively small area contact. At the same time, the flexibility in the perpendicular axis is used to precisely control the high-precision z-axis position in the mid-web section and isolate this positional control from that exerted in the lower precision up-web and down-web sections. The media is free to flex in the z-direction in the transition zones between the up-web and mid-web sections and between the mid-web and down-web sections, hence dramatically reducing the sensitivity of the z-axis behavior of the media in the precision zone to conditions outside the precision zone. The vertical cross section of the media transition between sections and the relative thicknesses of the air gaps are schematically illustrated in FIG. 4C.

In embodiments of the present invention, a compressed gas (typically air) and vacuum are used throughout stage operation in order to support, move, and constrain the media during inspection and repair. In some embodiments, the air cushion or gas bearing alone supports the media. No material substance is necessary in these embodiments. Different approaches are used in different parts of the instrument, tailored to the aforementioned selective differences in the accuracy desired for these parts.

Figure 5A:
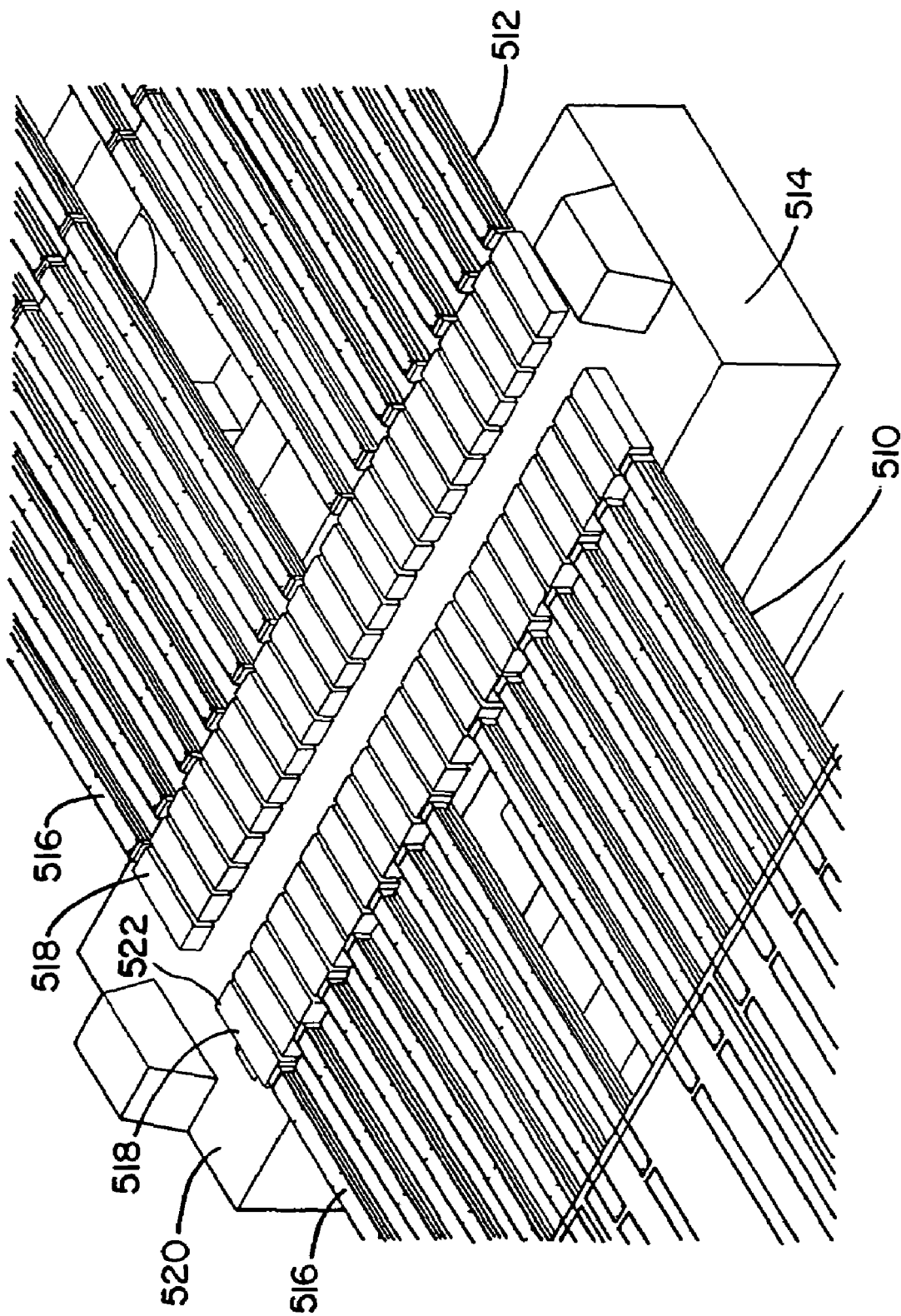
FIG. 5A is a detailed view of a central portion of a device according to an embodiment of the invention.

FIG. 5A illustrates a more detailed view of the low-precision up-web 510 and down-web 512 air tables surrounding the precision mid-web section 514 of an embodiment of the present invention. There are no demanding flatness tolerances for the media being handled on these up-web and down-web air tables. The purpose of these air tables is to support the glass so that it can be actuated by the two vacuum contacts, while maintaining a media elevation (air gap) sufficient to enable a safe transition from the up-web section to the precision mid-web section and from the mid-web section to the down-web section of the instrument. Compressed air is pumped out of a uniform array of air nozzles located in metal beams 516 placed along the x-axis span of the air tables to float the media at a pre-determined and safe elevation above the mechanical structure. In this embodiment, the reduced precision required for the air tables obviates the need to provide vacuum in the metal beams 516 placed along the x-span of the air tables. Alternative embodiments may incorporate the use of vacuum or other alternative techniques as needed. In some embodiments, the beams 516 are uniformly spaced along the x-axis span. A large (50 to 100 µm) air gap will enable a seamless transition between the low-precision air tables and the precision mid-web section and will reduce the tolerance requirements for the supporting frame structure. A benefit of the present invention is that in the air table sections, there is no need to precisely constrain the z-axis position of the floating media. However, at any given time, one vacuum contact from either the up-web and down-web sections can contact the media in the plane of the media (the x-y plane) to achieve movement of the media in the y-direction.

The precision mid-web section 514 of the assembly features a design that provides for precise control of the media position along the z-axis during inspection or repair. The present invention comprises two modes of operation, tailored to two closely related applications of the instrument, namely one in which the media is constantly in motion (e.g., Automated Optical Inspection) and the other in which the media moves in a stop-and-go fashion (e.g. Voltage Imaging Inspection or Array Repair). Depending on the mode of operation, this involves the use of both compressed air and vacuum, either concurrently or in a controlled vacuum/air cushion sequence.

Referring again to FIG. 5A, an embodiment is illustrated in which the transport and constraint sub-assembly of the precision mid-web section is specifically designed for an application in which the media is inspected while in motion. It should be noted that this motion does not necessarily have to be unidirectional, as the media is often moved using a back-and-forth scanning motion, making multiple passes under the imaging channels. For this mode of operation, a precision machined, vacuum pre-loaded air-cushion assembly is mounted on the reference surface 520 provided by the monolithic granite base plate. In one embodiment, for manufacturing convenience, this assembly comprises an array of pads 518 formed from a porous medium incorporating uniformly distributed vacuum nozzles 522. A variety of porous materials that can be machined to tight tolerances are suitable for use in this embodiment, including, but not limited to porous ceramics, foamed metals, porous glass, and synthetic porous materials. In one embodiment, the vacuum nozzles or ports are incorporated into the porous medium by first machining through holes in the porous medium. The holes in the porous medium are filled with an epoxy, thereby sealing the porous medium abutting the through holes. Sleeved through holes are created by subsequently re-drilling holes in the cured epoxy using a smaller diameter drill bit. Additional means of providing these ports which are sealed from the porous medium will be obvious to those skilled in the art. In a specific embodiment, the vacuum is introduced to the vacuum nozzles or ports by means of a trench extending across the granite base. The trench reduces the plumbing complexity and also acts as a plenum chamber equalizing the negative pressure (vacuum) for all the vacuum ports. In this embodiment, the distribution of vacuum nozzles within pads as well as adjustment of the vacuum/compressed gas pressures is used to optimize the air cushion uniformity and obtain an air cushion of the desired thickness.

Because of the nature of the porous medium used, the pressurized air is dispensed evenly throughout the entire surface of the pads, thus providing a means of generating a spatially uniform air cushion in which the lifting force exerted on the large flat media is accurately controlled while minimizing the use of pressurized air. As air exits through the top of the porous medium pads, floating the large flat media above the reference surface 520, the vacuum nozzles incorporated in the porous medium pads generate a vacuum pre-load to simultaneously pull the large flat media toward the reference surface 520. By this configuration, an air gap of 20 to 50 µm±2.5 µm is achievable. The pressurized air is supplied through pressurized air tubing, while the vacuum is applied by means of associated vacuum tubing. The combined effect of the air cushion and the vacuum pre-load provides precise control over the position of the media in the z-direction, while not applying any force or motion to the media in the plane of the media (the x-y plane).

In some embodiments, the porous medium pads 518 are aligned with each other. In the embodiment illustrated in FIG. 5A, the two arrays of porous pads located on either side of the precision mid-web section 514 constrain the position of the flat media to facilitate operation of imaging subsystems located on opposite sides of the gantry. In this particular embodiment, there are two imaging subsystems: Defect Detection Sub-system (DDS) and Defect Review Sub-system (DRS) and thus two pad arrays are used. In other embodiments, other pad configurations could be used, including a single pad mounted to reference surface 520.

It is not necessary that the pre-load be applied by vacuum from the bottom of the media being handled. Instead the pre-load may be provided by applying a static or dynamic pressure (for instance air pressure) from the top.

Figure 5B:
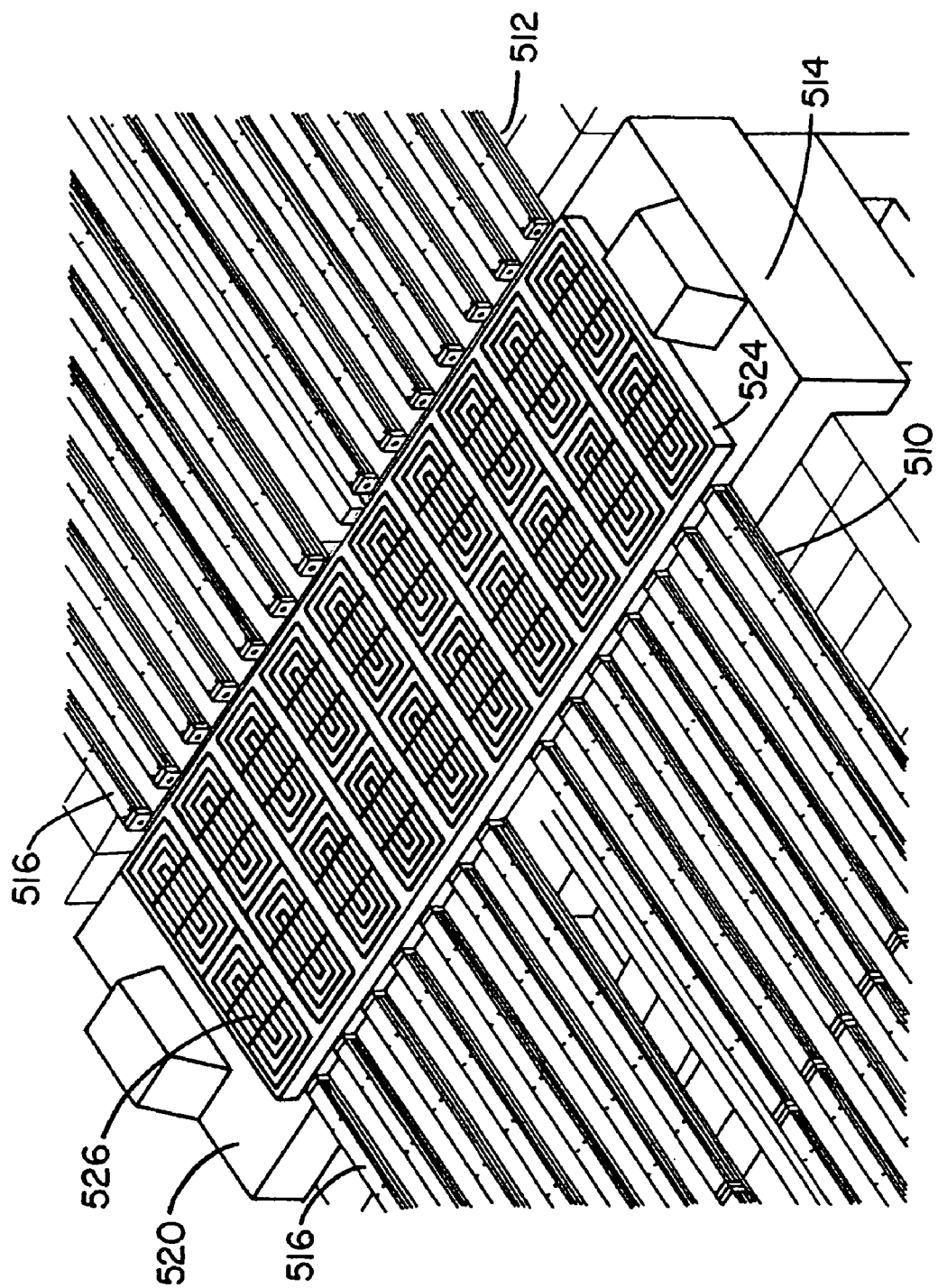
FIG. 5B is a detailed view of a central portion of a device according to another embodiment of the invention.

Another embodiment of the transport and constraint sub-assembly for the precision mid-web section is specifically designed for applications in which the media undergoes stop-and-go motion during either inspection or repair. This embodiment is illustrated in FIG. 5B. Again, it should be noted that this motion does not necessarily have to be unidirectional, as the media is often moved in a back-and-forth scanning motion making multiple passes under the imaging channels or the repair payload. The assembly consists of a rigid chuck 524 mounted on the reference surface 514 provided by the granite base plate. In this mode of operation, the media is alternately floated on an air cushion while the media is transported to a desired position or immobilized by vacuum on the rigid chuck surface during an inspection/repair step. Flotation of the flat media is accomplished through emission of a compressed gas through a plurality of orifices located in the upper surface of the rigid chuck. Vacuum is provided by creation of suction pressure using holes present in the rigid chuck in communication with distribution grooves 526.

The air cushion mode is used while the media is in motion to a new position and the vacuum chuck mode is used when the media is stopped for processing. Accordingly, the air cushion assembly is capable of providing on request, either an air-cushion used to float the flat media while it is transported to a desired location or vacuum used to immobilize the flat media during inspection or repair. The distribution grooves 526 formed in the rigid chuck 524 serve to provide orifices for both air cushion and vacuum operation.

Figure 6A:
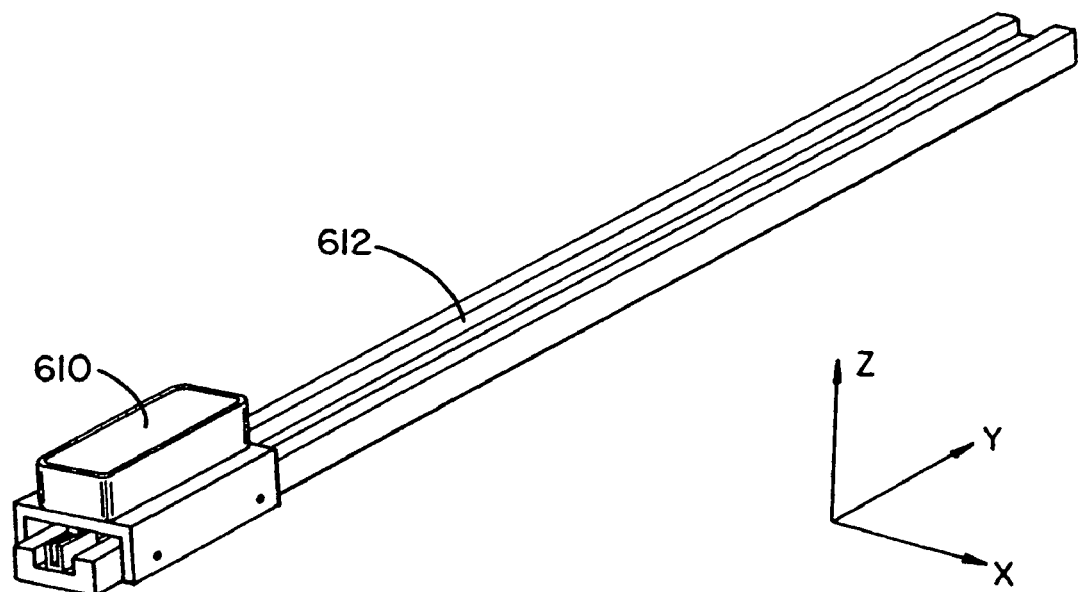
FIG. 6A is a perspective view of a transport element according to the invention.
Figure 6B:
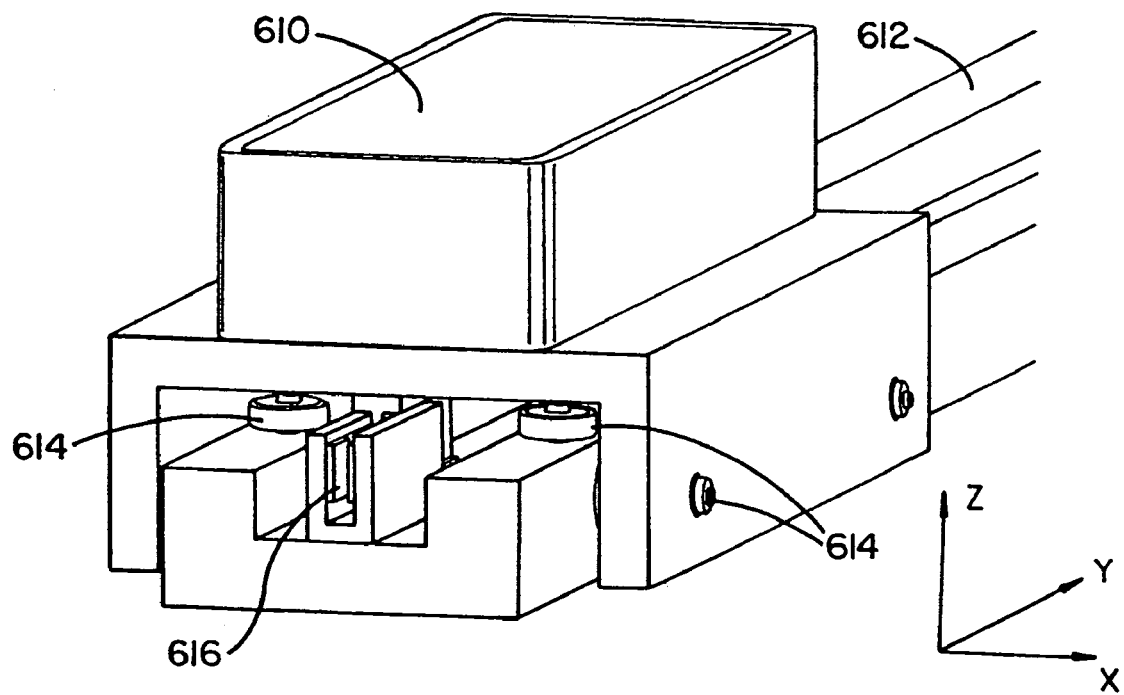
FIG. 6B is a close-up view of the transport element of FIG. 6A.

An embodiment of the invention comprises two vacuum contact assemblies 426 and 428 incorporated within the up-web and down-web sections (one vacuum contact per section) of the stage and placed specifically in the middle of the x-axis span of these sections. The vacuum contact assembly for one of the air tables is illustrated in FIGS. 6A and 6B. In the embodiment illustrated in FIGS. 6A and 6B, the vacuum contact assembly for the other air table is identical and is placed symmetrically in the other air table. The vacuum contact 610 is mounted on guiding beam 612 and moves along the beams in the y-direction. The support and linear motion of the contact is achieved by means of magnetically preloaded air bearings 614, linear servo motors 616, and associated linear encoders. At one end, the guiding beam is precision mounted to the granite base, which forms the precision mid-web section. Additionally, the beam is supported either continuously or at multiple points along the air table by the welded steel base frame. The beams themselves are typically made from either granite or extruded aluminum. In cases in which the beam is made from aluminum, the beam surfaces that interact with the air bearings are polished and hard anodized. Additionally, the beam is supported either continuously or at multiple points along the air table by the welded steel base frame. The beams themselves are typically made from either granite or extruded aluminum. In cases in which the beam is made from aluminum, the beam surfaces that interact with the air bearings are polished and hard anodized.

In some embodiments, the guiding beams on each stage are over two meters long. Therefore, in order to accommodate the differential thermal expansion between the beam and the supporting steel base frame, one end of each beam is allowed to float in the y-direction. To achieve this goal, the beam supports need to be flexible in the y-direction while being rigid in the x-z plane.

Because of the extended length of the guiding beams, it is expected that there will be a small amount of sagging in the z-direction along with some deviation from straightness in the x-direction. In an embodiment, these deviations are minimized by using a laser alignment jig to align the beam during mounting. The fact that the position of the media is precisely controlled in the measurement zone above the mid-web section, combined with the flexible nature of the inspected media, guarantees that the sag in the z-direction will not have a significant impact on the accuracy with which the z-position of the media is controlled in the precision mid section.

The two vacuum contacts operate in a coordinated up-web, down-web arrangement to allow a pipelined execution of media loading, media inspection/repair and media unloading operations. This pipelined operation overlaps part of the time required for loading/unloading (loading/unloading task time) with the inspection/repair task time, hence resulting in a savings in total time required by the instrument.

Figure 7A:
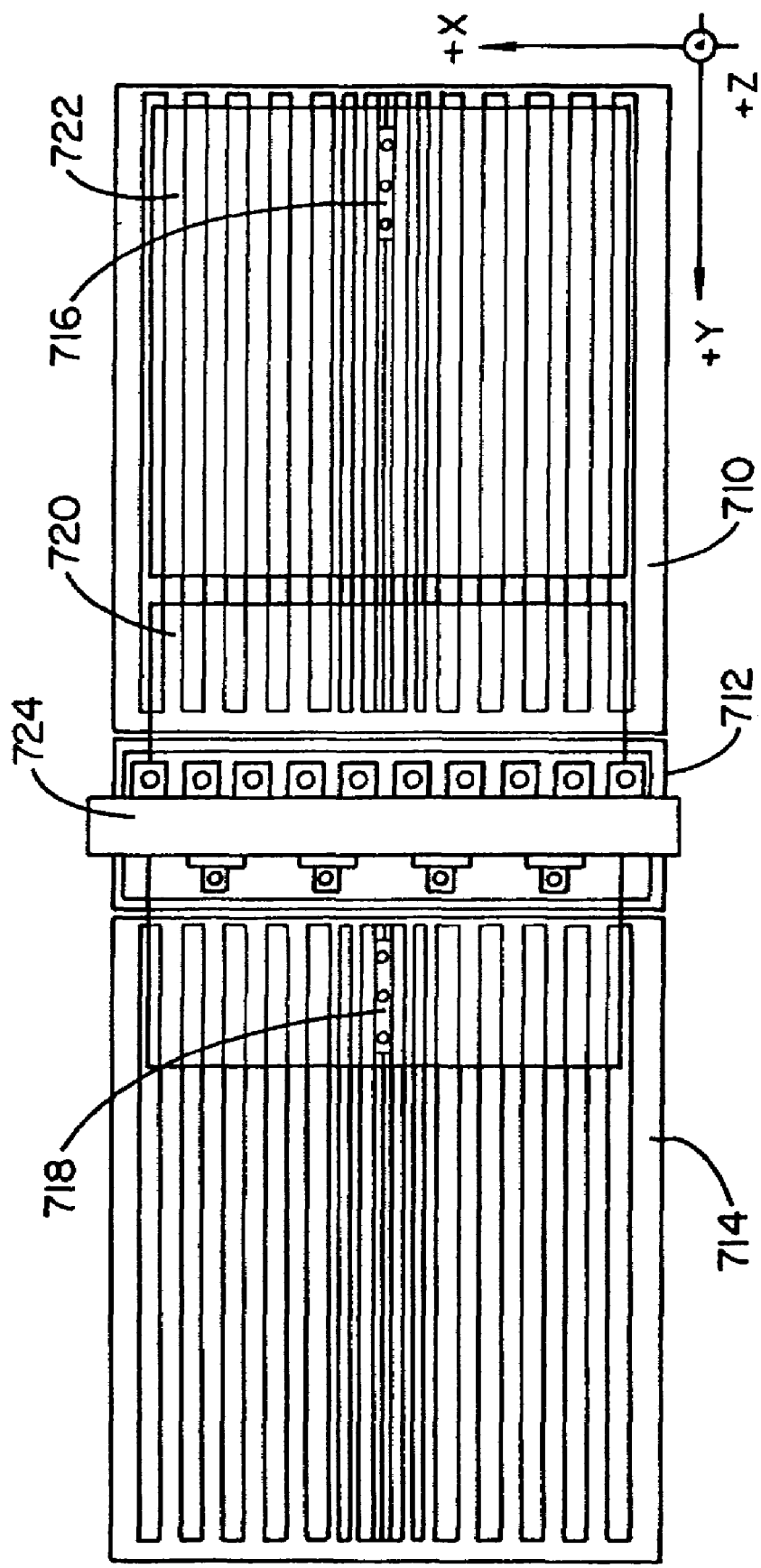
FIG. 7A is a top view of the apparatus illustrating a transport in a first position according to an embodiment of the invention.
Figure 7B:
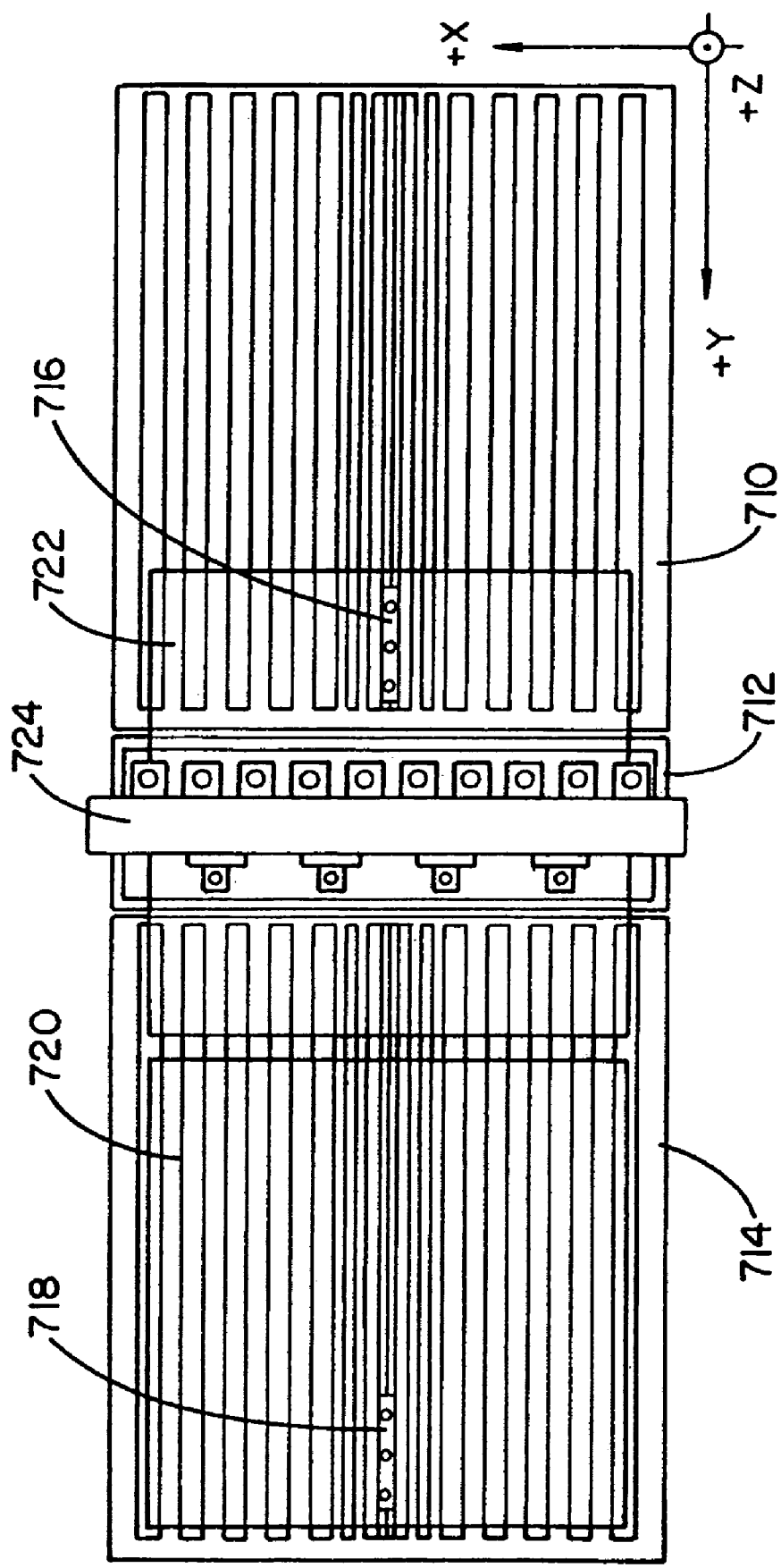
FIG. 7B is a top view of the apparatus illustrating a transport in a second position according to an embodiment of the invention.

The operation of the instrument in pipelined mode is illustrated schematically in FIGS. 7A and 7B, which depict two snapshots during pipelined operation. The operation is based on dividing the process of scanning of the entire surface of the media being inspected/repaired into a plurality of scanning operations performed in succession. Referring to FIG. 7A, the second contact 718 is holding panel 720, which is undergoing inspection/repair under the system gantry 724. While the second half (right half) of the media panel 720 is being inspected/repaired, a new media panel 722 is loaded on to the up-web air table 710. The new media panel 722 is scrubbed and squared (considered part of the loading time) and then contacted by the first vacuum contact 716. The new media panel 722 then waits while the second half processing of the previous media panel 720 is completed. Upon completion of processing, the second contact 718 then moves the finished media panel 720 out of the mid-web section 712 and completely onto the down-web air table 714. Simultaneously, the first contact 716 moves the new media panel 722 into the mid-web section, where the processing of the first half (left half) of media panel 722 begins. Concurrent with the first half processing of the new media panel 722, the previous panel 720 can be unloaded from the system.

In FIGS. 7A and 7B the instrument is depicted as being symmetric. However, symmetry is not an inherent requirement. The illustration shown is for a plant configuration in which concurrent robot loading and robot unloading is the means for transporting media to and from the system. However, in a case in which the instrument is directly linked to a down-web plant conveyor, the down-web section of the instrument may be shortened by removing the air table span where the media waits for the robot pick-up. In this alternative case, the processed media will immediately be transferred onto the plant conveyor and leave the system as the new media is brought in. This could result in an instrument embodiment as previously illustrated in FIG. 4A. In embodiments in which the scrubbing and squaring of the glass is considered part of the instrument's functionality, the same table shortening cannot be done for the up-web air table.

Figure 7C:
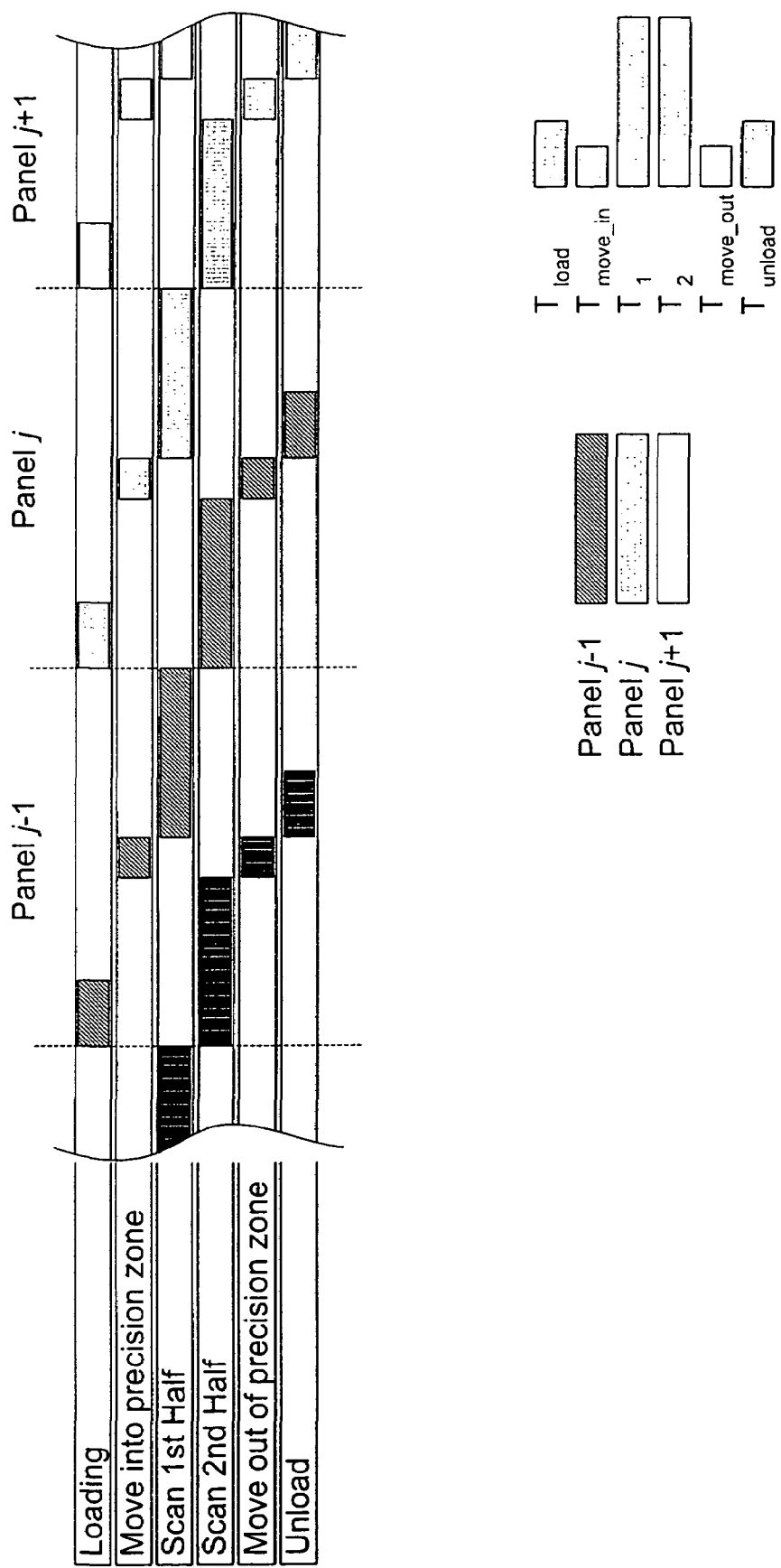
FIG. 7C is a timeline for the apparatus illustrating the pipeline mode of operation for a transport according to an embodiment of the invention and which serves as a flow chart for instruction in programming the system according to the invention.

The pipelined operation described above and the time overlap between the involved sub-steps are illustrated with the timing diagram in FIG. 7C. From the figure, it can be seen that, while the sequential operation has a tact time of $$T_{seq} = T_{load} + T_{move\_in} + T_1 + T_2 + T_{move\_out} + T_{unload}, \quad (1)$$

the pipelined operation has a reduced tact time of $$T_{pipe} = T_{move\_in} + T_1 + T_2. \quad (2)$$

FIG. 7C illustrates that in this embodiment of pipelined operation, the time required to load, unload and move the panels out of processing zone ("move out") is eliminated from the tact time once the pipeline is filled and media stream in and out of the stage.

Tact time is of significant importance for the customers of this type of instrument. Improving the throughput of the system and keeping the system utilization near a maximum level adds significant value to the instrument. Pipelined operation ensures that in an in-line operating mode, the utilization of the processing zone is kept close to 100%.

The thickness variation in the media being inspected (e.g. glass panels) often reaches 30 µm and exceeds the controlled air gap thickness (vacuum pre-loaded air cushion) variation of ±2.5 µm of the precision mid-web section. Additionally, these variations are beyond the ±1 µm depth-of-field characteristic of the high resolution defect review imaging channels. However, the rate of thickness change (variations) typically is less than 10 µm over 40 mm. To compensate for these low spatial frequency thickness variations, in one embodiment, fast tracking auto-focus hardware is incorporated into the stage's high-resolution defect review payloads to keep the channels in sharp focus. Furthermore, because in AOI applications the stage motion is not stopped for image acquisition, strobe illumination is used to freeze the motion and acquire non-blurred images from these high-resolution area scan imaging channels.

As mentioned previously, a drawback of the design used for conventional stages has been the monolithic nature of the entire stage. Accordingly, embodiments of the present invention features a monolithic granite precision block that is significantly reduced in size. Additionally, in this embodiment, the main building blocks of the stage, namely the precision mid-web section and the surrounding low-precision, up-web and down-web air tables, are transported and shipped separately. More specifically, the stage design comprises modular sub-blocks which are assembled and pre-aligned at the factory. The modular sub-blocks are then disassembled and transported in disassembled form to the customer site. Upon delivery, the modular sub-blocks are re-assembled at the customer plant into the final instrument configuration.

Figure 8:
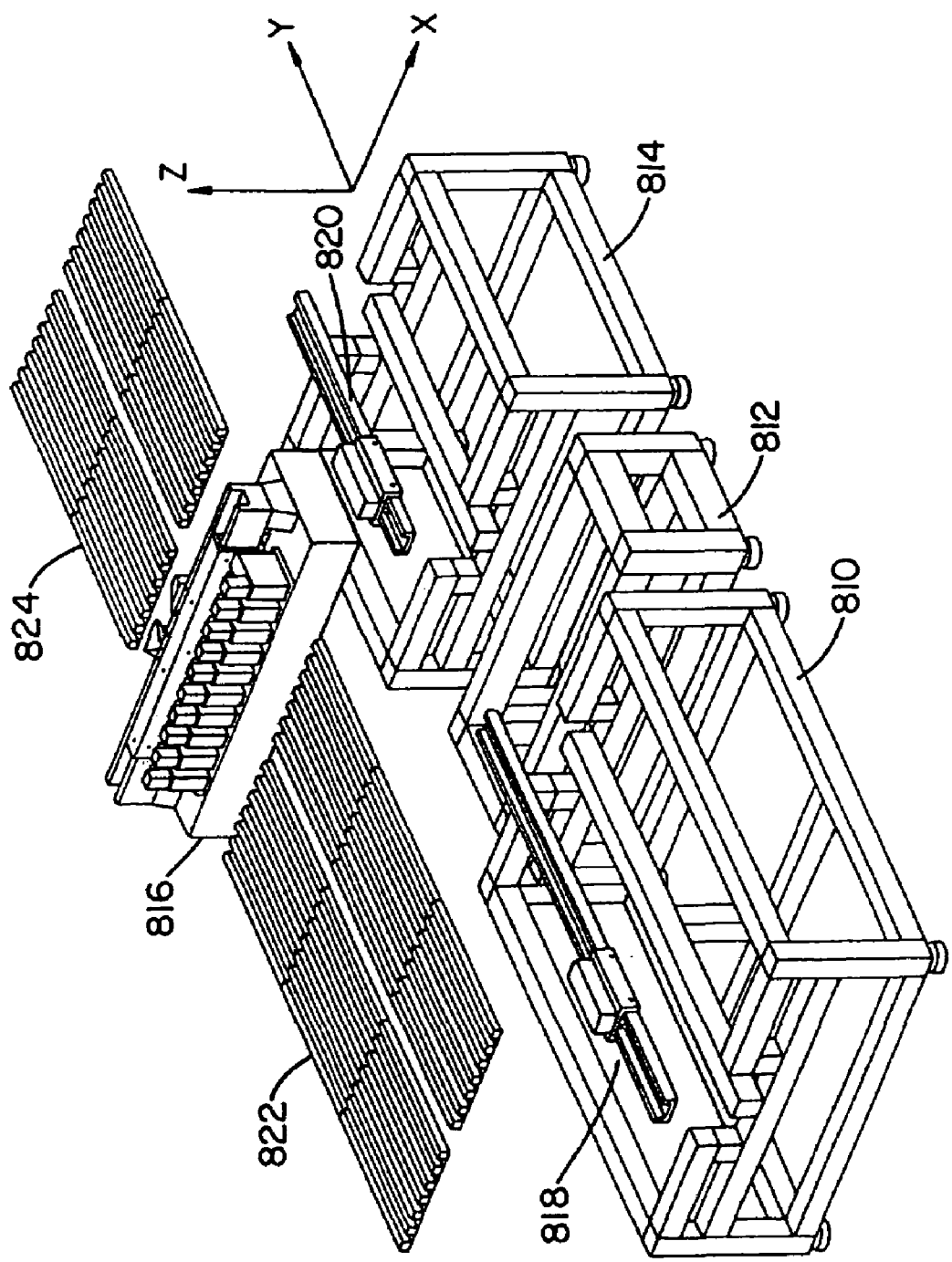
FIG. 8 is an illustration of the modular design featured in an embodiment of the present invention.

FIG. 8 schematically illustrates the modular design of an embodiment of the present invention, which comprises individual stage components. The design comprises the following separable components:

Three welded steel base frames for up-web 810, mid-web 812 and down-web 814 sections;

Gantry sub-assembly with granite base 816;

Two y-axis linear servo motor assemblies (up-web 818 and down-web 820) with vacuum contacts;

Two air tables (up-web 822, down-web 824). The size of the down-web air table is determined by the plant layout and the mode of operation (robot loading/unloading versus in-line operation)

The welded steel base frames provides a rigid mounting base for all of the system components. They are designed to rigidly carry a distributed load in the z-direction as well as to resist shear forces in the x-y plane (the shear forces are introduced by the motion of the instrument payloads). The base frames, however, are not designed to resist deformations due to localized forces (for instance lifting the frame by one corner). The steel base frames attains their required rigidity in conjunction with the foundation to which they are attached. The frames need to be carefully leveled and care needs to be taken to assure firm contact of all the mounting feet with the foundation. The mounting feet are equipped with passive, polymer dampers designed to dissipate higher frequency (>15 Hz) vibrations. The dampers work in two ways: to protect the system from shock and vibration transmitted through the foundations as well as to protect the foundations from vibrations introduced by the system. Even though the steel base frames may be large (at least 2.0×4.0× 0.5 meters) they are light enough for air transport. To further facilitate system transportation, the frames may be split into three separate subassemblies: the base for the gantry assembly and two bases for the air tables. The subassemblies may be packaged separately and then combined at the system installation site.

The gantry sub-assembly comprises the granite base, the granite gantry with optical payloads, linear servo motors, and linear encoders to move the payloads along the x-axis. In the embodiment according to the present invention illustrated in FIG. 5A, the precision surface is formed by the vacuum pre-loaded air chuck. In the embodiment illustrated in FIG. 5B, the precision surface is formed by the alternating air cushion/vacuum chuck. Precision components of the system are located around the gantry sub-assembly, which is designed for high precision in comparison to the lower precision air tables. The granite base and gantry serve as a reference for assembly of the entire stage system: Its top surface provides a precision reference surface for mounting the y-axis guides and linear motors; the front and back surfaces are equipped with specialized mounting hardware enabling precise positioning of the up-web and down-web air tables. Since the mass of the actuated media is much smaller than the mass of the rigid chuck, the gantry assembly may be considerably lighter than those in conventional stage designs. However, the gantry assembly is typically at least an order of magnitude heavier than the payloads installed on the gantry. This helps to balance out and dissipate the reaction forces generated by acceleration and/or deceleration of the payloads.

The remaining components of the stage are the up-web and down-web air tables and the associated y-axis linear servo motor assemblies, which were previously discussed in detail.

This modular design provides at least two significant advantages over conventional designs. First, it provides significant cost benefits in handling and transportation of the stage. Secondly, it provides a design that is easily adapted to perform closely related tasks in an application domain. For example, the task of TFT/LCD inspection by different imaging technologies as well as the task of TFT/LCD repair can be accommodated with relative ease.

The invention has been explained with respect to specific embodiments. Other embodiments will be evident to those of ordinary skill in the art. Therefore, the invention should not be considered limited by the disclosure and should only be considered as limited as defined by the appended claims.

What is claimed is:

1. A split-axis stage in a flat panel inspection system suitable for inspection of large, substantially planar, thin, flexible media, the media comprising elements of TFT LCD arrays, the stage comprising:

a first section operative to position the media with a first handling precision and to transport the media in a first direction;

a second section physically coupled to the first section, the second section operative to receive the media from the first section, to position the media with a second handling precision, and to transport the media further in the first direction, only the second section including a stable and rigid support structure such that the second handling precision is more precise than the first handling precision; and instrumentation mounted to the second section, the instrumentation being operative to characterize physical attributes of elements of the media received by the second section from the first section.

2. The inspection system stage according to claim 1 wherein the first section is modular and the second section is modular and removably connectable to the first section, and wherein the support structure of the second section comprises a granite slab.

3. The inspection system stage according to claim 2 wherein the handling precision of the second section is enhanced by the stability of the granite slab to be sufficient to controllably position the media within a final tolerance.

4. The inspection system stage according to claim 3 wherein the final tolerance in the direction orthogonal to a plane parallel to an upper surface of the second section to within 2.5 µm of any selected lateral position.

5. The inspection system stage of claim 1 wherein characterizing physical attributes of the media is performed during continuous translation of the media through said second section.

6. The inspection system stage of claim 1 wherein characterizing physical attributes of the media is performed while holding the media stationary and then subsequently translating the media.

7. The inspection system stage of claim 1 wherein media surface height compensation is of less than 10 µm over 40 mm to adjust for thickness variations in the media.

8. The inspection system stage of claim 1 wherein the second section comprises an assembly of the second section for producing a field of controllable gas emission, and includes a mechanism that produces further both a vacuum at selected locations of the section and a second pressurized gas bearing in the field in order to controllably suspend and vertically position the media.

9. The inspection system stage of claim 1 wherein the field producing assembly comprises a porous medium.

10. The inspection system stage of claim 1 wherein the porous medium is selected from the group consisting of porous ceramics, foamed metals, porous glass, and synthetic porous materials.

11. The inspection system stage of claim 1 wherein the producing mechanism comprises vacuum ports integrated with the porous medium.

* * * * *